United States Patent [19]

Avidan et al.

[11] Patent Number: 4,547,616

[45] Date of Patent: Oct. 15, 1985

[54] CONVERSION OF OXYGENATES TO LOWER OLEFINS IN A TURBULENT FLUIDIZED CATALYST BED

[75] Inventors: Amos A. Avidan, Mantua; Ronald M. Gould, Sewell; Steven E. Kane, Paulsboro, all of N.J.

[73] Assignee: Mobil Oil Corporation, New York, N.Y.

[21] Appl. No.: 687,045

[22] Filed: Dec. 28, 1984

[51] Int. Cl.$^4$ ............................................... C07C 1/20
[52] U.S. Cl. ...................................... 585/640; 585/639
[58] Field of Search ....................... 585/640, 639, 638

[56] References Cited

U.S. PATENT DOCUMENTS

| | | | |
|---|---|---|---|
| 3,894,106 | 7/1975 | Chang et al. | 585/469 |
| 3,894,107 | 7/1975 | Butter et al. | 585/469 |
| 3,928,483 | 12/1975 | Chang et al. | 585/469 |
| 4,025,572 | 5/1977 | Lago | 585/640 |
| 4,025,575 | 5/1977 | Chang et al. | 585/640 |
| 4,025,576 | 5/1977 | Chang et al. | 585/640 |
| 4,025,579 | 5/1977 | Gruber et al. | 585/640 |
| 4,052,479 | 10/1977 | Chang et al. | 585/640 |
| 4,083,889 | 4/1978 | Caesar et al. | 585/640 |
| 4,238,631 | 12/1980 | Daviduk et al. | 585/469 |
| 4,338,475 | 7/1982 | Pennington et al. | 585/640 |
| 4,361,715 | 11/1982 | Short et al. | 585/640 |
| 4,423,274 | 12/1983 | Daviduk et al. | 585/640 |
| 4,431,856 | 2/1984 | Daviduk et al. | 585/639 |

FOREIGN PATENT DOCUMENTS 0081683 11/1982 European Pat. Off. ............ 585/640

Primary Examiner—D. E. Gantz
Assistant Examiner—A. Pal
Attorney, Agent, or Firm—A. J. McKillop; M. G. Gilman; L. G. Wise

[57] ABSTRACT

Conversion of oxygenates to lower olefins is improved by operating a fluidized bed of zeolite catalyst in a turbulent fluidization regime at elevated temperature and controlled catalyst activity.

9 Claims, 5 Drawing Figures

CONVERSION OF OXYGENATES TO LOWER OLEFINS IN A TURBULENT FLUIDIZED CATALYST BED

BACKGROUND

This invention relates to a technique for converting oxygenated aliphatic compounds, such as methanol or dimethyl ether, to lower olefins. In particular, it provides an efficient continuous process for producing an olefinic product rich in $C_3+$ alkenes, while minimizing byproduct aromatics and ethene. In view of the availability and low cost of synthetic methanol (MeOH) and its corresponding dehydration product dimethylether (DME), primary emphasis will be placed on these oxygenates in the following description of the methanol-to-olefin (MTO) process.

Various zeolitic catalysts are useful for converting methanol and other lower aliphatic alcohols or corresponding ethers to olefins. Recent interest has been directed to a catalytic process for converting methanol over ZSM-5 catalysts and related to valuable hydrocarbons rich in ethene and $C_3+$ alkenes. Various processes are described in U.S. Pat. Nos. 3,894,107 (Butter et al); 3,928,483; 4,025,575; 4,252,479 (Chang et al); 4,025,572 (Lago); and in copending U.S. patent application Ser. No. 388,768, filed June 15, 1982 (Yurchak et al), incorporated herein by reference. Significance of the methanol-to-olefins (MTO) type processes, especially for producing ethene, is discussed in *Hydrocarbon Processing*, November 1982, pp. 117-120. It is generally known that MTO processes can be optimized to produce a major fraction of $C_2-C_4$ olefins; however, a significant $C_5+$ byproduct may be coproduced, including polymethylbenzenes such as durene, as described in U.S. Pat. No. 4,025,576 (Chang et al). Prior process proposals have included a separation section to recover ethene and other gases from byproduct water and $C_5+$ hydrocarbon liquids.

Fluidized bed MTO processes provide an important economic unit in the synthesis route for producing various chemicals, fuels and other hydrocarbon products from coal and/or natural gas. As disclosed in copending U.S. patent application Ser. No. 548,377 filed Nov. 3, 1983 (Tabak) and Ser. No. 598,955 filed Apr. 11, 1984 (Hsia et al), incorporated herein by reference; methanol, DME or the like may be converted to liquid fuels, particularly distillate, in a multi-stage continuous process, with integration between the major process units. The initial stage MTO process hydrocarbon olefins effluent can be fed to a catalytic oligomerization unit. Although the $C_3+$ mono-olefins are readily converted by ZSM-5 type acid zeolites to produce olefinic oligomers, ethene tends to be less reactive at moderate temperature, and may be removed from the oligomerization system. Thus, minimizing ethene production and increasing $C_3+$ olefin in the MTO product stream is advantageous, and this is a main object of the present invention.

SUMMARY OF THE INVENTION

A process has been found for continuous conversion of oxygenated feedstock to hydrocarbon products consisting predominately of lower olefins wherein the feedstock is contacted at elevated temperature with a turbulent fluidized bed of zeolite catalyst under conversion conditions. The improvement herein comprises maintaining the fluidized catalyst bed in a vertical reactor column having a turbulent reaction zone by passing feedstock vapor upwardly through the reaction zone at a velocity greater than dense bed transition velocity to a turbulent regime and less than transport velocity for the average catalyst particle. A portion of coked catalyst is withdrawn from the reaction zone. By oxidatively regenerating the withdrawn catalyst and returning regenerated catalyst to the reaction zone at a rate to control catalyst activity, propane:propene molar ratio in the hydrocarbon product is maintained at about 0.04:1 to 0.1:1 under conditions of substantially complete feedstock conversion, and $C_3+$ olefin production is optimized.

These and other features of the invention will be seen in the following description and drawings.

THE DRAWINGS

DESCRIPTION OF THE PREFERRED EMBODIMENTS CATALYSTS

Figure 1:
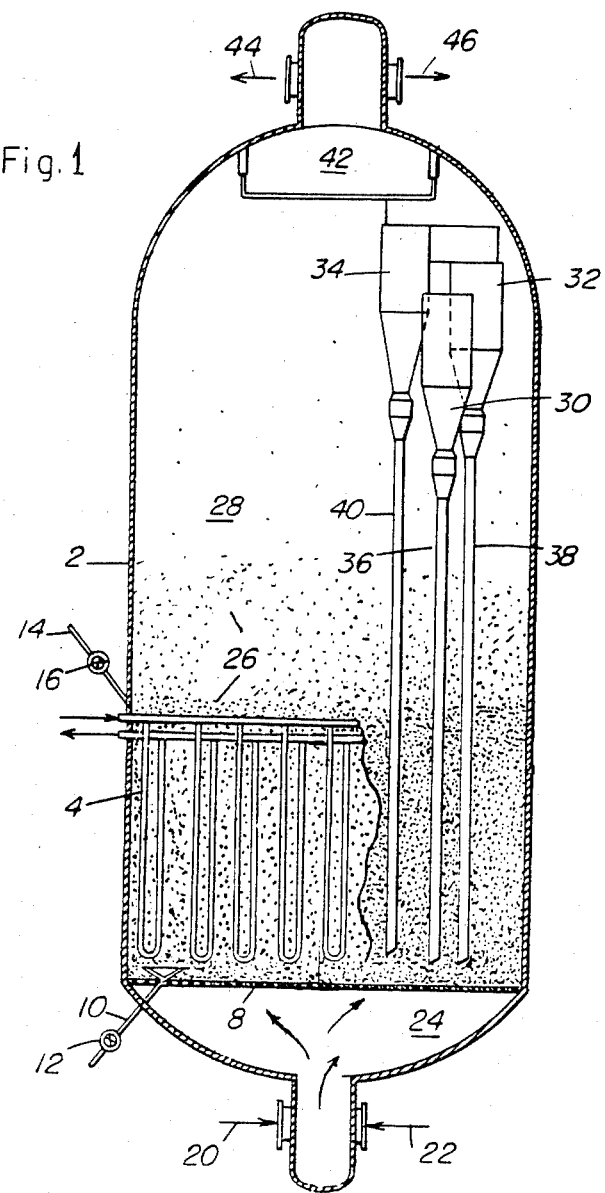
FIG. 1 is a schematic view of a fluidized bed reactor system according to the present invention.

Catalyst versatility permits the same zeolite to be used in both methanol dehydration and olefin formation. While it is within the inventive concept to employ substantially different catalysts in plural stages, it is advantageous to employ a standard ZSM-5 having a silica alumina molar ratio of 70:1 or greater in a once-through fluidized bed unit to convert 98 to 100 percent, preferably at least 99.5 percent, of the feedstock oxygenate.

The MTO catalysts preferred for use herein include the crystalline aluminosilicate zeolites having a silica to alumina ratio of at least 12, a constraint index of about 1 to 12. Representative of the ZSM-5 type zeolites are ZSM-5, ZSM-11, ZSM-12, ZSM-22, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of all patents cited herein are incorporated herein by reference. These medium pore shape selective catalysts are sometimes known as porotectosilicates or "Pentasil" catalysts.

Other catalysts and processes suitable for converting methanol/DME to lower olefins are disclosed in U.S. Pat. No. 4,393,265 (Bonifaz), U.S. Pat. No. 4,387,263 (Vogt et al) and European Patent Application Publ. No. 0081683 (Marosi et al). ZSM-34 and ZSM-45 are known MTO catalysts, as disclosed in U.S. Pat. No. 4,086,186 (Rubin et al) and European Patent Application No. 83305747.4 (Rosinski et al), respectively. In addition to the preferred aluminosilicates, the borosilicate, ferrosilicate and "silicalite" materials may be employed.

ZSM-5 type pentasil zeolites are particularly useful in the MTO process because of their regenerability, long life and stability under the extreme conditions of MTO operations. Usually the zeolite crystals have a crystal size from about 0.02 to 2 microns or more, with large crystals greater than 1 micron being preferred. In order to obtain the desired particle size for fluidization in the turbulent regime, the zeolite catalyst crystals are bound with a suitable inorganic oxide, such as silica, alumina, etc. to provide a zeolite concentration of about 5 to 90 wt. %. In the description of preferred embodiments a 40% ZSM-5 catalyst calcined wih 60% $Al_2O_3$ is employed unless otherwise stated.

Particle size distribution can be a significant factor in achieving overall homogeneity in the fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 40 microns. This class of fluidizable particles is classified as Geldart Group A. Accordingly, the fluidization regime is controlled to assure operation between the transition velocity and transport velocity. Fluidization conditions are substantially different from those found in non-turbulent dense beds (e.g., U.S. Pat. No. 4,423,274) or transport beds.

PROCESS OPERATION

Referring now to FIG. 1, a reactor vessel 2 is shown provided with heat exchange tube means 4. There may be several separate heat exchange steam generating tube bundles so that temperature control can be separately exercised over different portions of the fluid catalyst bed. The bottoms of the tubes are spaced above a feed distributor grid 8 sufficiently to be free of jet action by the charged feed through the small diameter holes in the grid. Provision is made for withdrawing catalyst from above grid 8 as by conduit means 10 provided with flow control valve 12 for passage to catalyst regeneration. Provision is also made for passing the partially regenerated catalyst to the reactor fluid bed of catalyst as by conduit means 14 provided with flow control valve 16. The regenerated catalyst is charged to the catalyst bed beneath the upper interface and sufficiently below to achieve good mixing in the fluid bed. Since the amount of regenerated catalyst passed to the reactor is small by comparison, the temperature of the regenerated catalyst does not upset the temperature constraints of the reactor operations in a significant amount.

The methanol feed with or without diluent may be charged through one or more openings 20 and 22 in a bottom extended portion of the reactor. The methanol in liquid condition can be sprayed by suitable means into the bed above the grid. The charged methanol feed in vaporous condition enters the vessel by inlet means 20 and 22 in open communication with chamber 24 beneath grid 8. The charged methanol passes through reactant distributor grid 8 and into the bed of catalyst thereabove at a velocity sufficient to form a generally upwardly flowing suspension of reactant and reaction product with the catalyst particles.

A plurality of sequentially connected cyclone separator means 30, 32 and 34 provided with diplegs 36, 38 and 40 respectively are positioned in an upper portion of the reactor vessel comprising dispersed catalyst phase 28.

The product effluent of methanol conversion separated from catalyst particles in the cyclone separating system then passes to a plenum chamber 42 before withdrawal therefrom by one or more opening means 44 and 46. The product effluent recovered by openings 44 and 46 is cooled and separated in means not shown to recover liquid hydrocarbons, gaseous material and formed water comprising some catalyst fines. Since conversion of the methanol is at least 95% and preferably at least 99.5%, the water phase with unreacted methanol need not be processed to recover unreacted methanol. The recovered hydrocarbon product comprising olefins and/or aromatics, paraffins and naphthenes is thereafter processed as required to provide a desired gasoline or higher boiling product.

Under optimized MTO conditions the turbulent bed has a superficial vapor velocity of about 0.3 to 2 meters per second (m/sec). At higher velocities entrainment of fine particles may become excessive and beyond 10 m/sec the entire bed may be transported out of the reaction zone. At lower velocities, the formation of large bubbles can be detrimental to conversion. Even fine particles cannot be maintained effectively in a turbulent bed below about 0.1 m/sec.

A convenient measure of turbulent fluidization is the bed density. A typical turbulent bed has an operating density of about 100 to 300 $kg/m^3$, measured at the bottom of the reaction zone, becoming less dense toward the top of the reaction zone due to pressure drop and particle size differentiation. This density is generally between the catalyst concentration employed in dense beds and the dispersed transport systems. Pressure differential between two vertically spaced points in the reactor column can be measured to obtain the average bed density at such portion of the reaction zone. For instance, in a fluidized bed system employing ZSM-5 particles having a clean apparent density of 1.06 gm/cc and packed density of 0.85, an average fluidized bed density of about 190 to 200 $kg/m^3$ is satisfactory. By virtue of the turbulence experienced in the turbulent regime, gas-solid contact in the catalytic reactor is improved, providing substantially complete conversion and enhanced selectivity. One main feature of this concept is the inherent control of bubble size and characteristic bubble lifetime. Bubbles of the gaseous reaction mixture are small, random and short-lived, thus resulting in good contact between the gaseous reactants and the solid catalyst particles.

A significant difference between the process of this invention and the oxygenate conversion processes of the prior art is that operation in the turbulent fluidization regime is optimized to produce $C_3^+$ lower olefins. Another advantage of operating in such a mode is the control of bubble size and life span, thus avoiding large scale gas by-passing in the reactor. The process of the present invention does not rely on internal baffles in the reactor for the purpose of bubble size control such as the baffles which are employed in the prior art dense bed processes discussed above.

Figure 2:
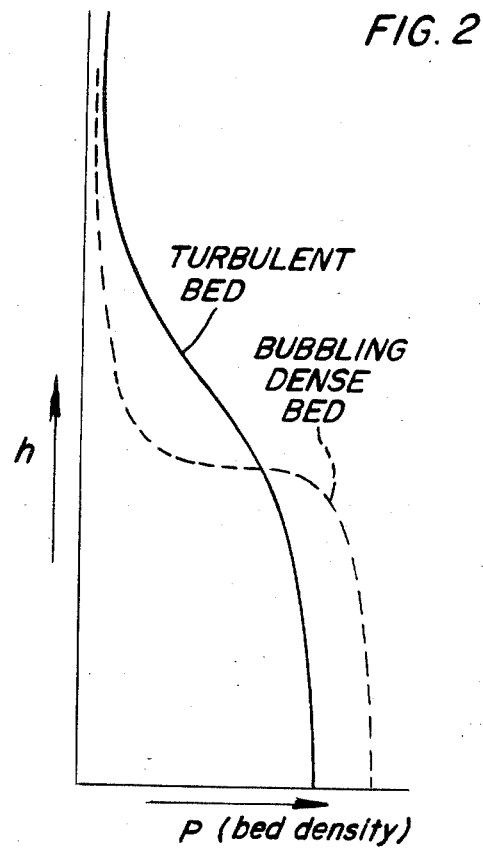
FIG. 2 is a graphic plot of typical catalyst distribution in a vertical reactor.

Fluidization is a gas-solid contacting process in which a bed of finely divided solid particles is lifted and agitated by a rising stream of gas. Fluidization occurs in a bed of particulates when an upward flow of fluid through the interstices of the bed of particles attains a pressure differential and frictional resistance increment exceeding particulate weight. At this point of minimum fluidization, an increase in the fluid rate lifts or supports the particles. This condition is referred to as incipient bouyancy, since at this fluid rate, the particles are still so close as to have essentially no mobility. Where it is desired to create bed homogeneity, the fluid velocity can be increased to the point of blowing bubbles or voids into the bed which is then violently mixed as the bubbles rise. The increased fluid velocity at which bubbles first form is called the incipient-bubbling velocity. The differences between a bubbling dense bed and turbulent bed can be visualized by referring to FIG. 2, which depicts a typical bed density profile for a low velocity dense bed (dashed line), having a fairly sharp break at a vertical point in the reactor. By contrast the turbulent bed (solid line) density ($\rho$) decreases at a more even rate with upward bed height (h).

In the past research workers tested a wide variety of materials to study the fluidization effects thereon. However, the conclusions drawn from data on the fluidization of one particulate matter were not found to be applicable to other powders which had quite different particle sizes and densities. Geldart [7 *Powder Technology* 285 (1973)] reports that the behavior of solids fluidized by gases falls into four clearly recognizable groups, characterized by the difference in density between the particular particles and the fluidizing fluid and the mean size of the particles. Powders in Geldart's group A exhibit a dense phase expansion after minimum fluidization and prior to the commencement of bubbling, group B powders bubble at the minimum fluidization velocity; the powders in group C are difficult to fluidize at all and those in group D can form stable spouted beds. Particles useful in the present invention as well as fluid catalytic cracking catalysts are typical group A powders, usually having a small mean size and/or a low apparent particle density (e.g. less than about 1.4 g/cm$^3$). These powders expand considerably before bubbling commences. As the superficial gas velocity is increased in the dense bed, eventually slugging conditions occur and with a further increase in the superficial gas velocity the slug flow breaks down into a turbulent regime. The transition velocity at which this turbulent regime occurs appears to decrease with particle size. The turbulent regime extends from the transition velocity to the so-called transport velocity. (Yerushalmi et al, *Further Studies of the Regimes of Fluidization*, 24 Powder Tech. 187-205 (1979). As the transport velocity is approached, there is a sharp increase in the rate of particle carryover, and in the absence of solid recycle, the bed could empty quickly.

The transition from bubbling dense bed to turbulent fluidization involves a gradual breakdown of large bubbles into small bubbles and voids, providing a progressive change toward a condition of greater homogeneity. Solid mixing is vigorous, the interaction of the two phases is strong, and the contact between gas and solid is highly efficient.

Since the fluidized bed of zeolite catalyst of the present invention is operated in the turbulent regime, the gaseous reaction mixture is present as small dispersed bubbles whose existence is extremely short. The bubbles travel only a few feet as they constantly break-up, coalesce and reform. Therefore when practicing the present conversion process it is unnecessary to provide baffles in the reactor vessel as is often found necessary to control the large bubbles encountered in bubbling dense fluidized beds, such as those employed in the prior art processes.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6-2 g/cc, preferably 0.9-1.6 g/cc. The catalyst particles can be in a wide range of particle sizes up to about 250 microns, with an average particle size between about 20 and 100 microns, preferably in the range of 10-150 microns and with the average particle size between 40 and 80 microns. When these solid particles are placed in a fluidized bed where the superficial fluid velocity is 0.3-2, meters/sec. MTO operation in the turbulent regime is obtained. The velocity specified here is for an operation at a total reactor pressure of about 100 to 300 kPa. Those skilled in the art will appreciate that at higher pressures, a lower gas velocity may be employed to ensure operation in the turbulent fluidization regime.

The reactor can assume any technically feasible configuration, but several important criteria should be considered. The bed of catalyst in the reactor can be at least about 5-20 meters in height, preferably about 9 meters. Fine particles may be included in the bed, especially due to attrition, and the fines may be entrained in the product gas stream. A typical turbulent bed may have a catalyst carryover rate up to about 1.5 times the reaction zone inventory per hour. If the fraction of fines becomes large, a portion of the carryover can be removed from the system and replaced by larger particles. It is preferred to have a fine particle separator, such as a cyclone or filter means, disposed within the reactor shell to recover catalyst carryover and return this fraction continuously to the bottom of the reaction zone for recirculation at a rate of about one catalyst inventory per hour.

EXAMPLES 1-3

A series of continuous methanol conversion runs are conducted in a vertical reactor vessel under turbulent fluidized bed conditions using ZSM-5 catalyst ($\alpha=15$) having about 3 to 36 wt. % coke deposited by prior conversion processes. The reactor is a vertical column having a turbulent reaction zone about 9 meters in height and containing catalyst with an average particle size of 75 to 80 microns. The fines less than 40 microns can vary from about 15 to 25 wt. %, and less than 20 microns from 3 to 7%. The results are tabulated below:

TABLE I

| Example - Run No. | 1 | 2 | 3 |
|---|---|---|---|
| Temp °C. | 484 | 478 | 500 |
| Pressure, kPa | 185 | 205 | 200 |
| Methanol partial pressure, kPa | 185 | 105* | 200 |
| WHSV (MEOH:ZSM-5)** | 2.8 | 1.5 | 2.6 |
| RI (propane:propene mole ratio) | 0.08 | 0.1 | 0.065 |
| Time on stream (days) | 25 | 25 | 17 |
| Vapor velocity (m/sec.) | 1.7 | 1 | 1.7 |
| Olefins: | | | |
| Ethene | 5.0 | 6.5 | 5.2 |
| Propene | 29.8 | 30.2 | 33.0 |
| Butenes | 18.7 | 21.8 | 19.1 |
| Pentenes | 10.7 | 9.5 | 12.0 |

TABLE I-continued

| Example - Run No. | 1 | 2 | 3 |
|---|---|---|---|
| (C$_2$-C$_5$) | (64.2) | (68.0) | (69.3) |
| C$_6$ | 4.4 | 2.9 | 4.8 |
| C$_7$ | 1.9 | 2.9 | 4.8 |
| Others | 2.8 | 1.5 | 1.8 |
| (Total Olefins) | (73.3) | (74.1) | (77.1) |
| C$_3$+:C$_2$ olefin ratio | 13.7:1 | 10.4:1 | 13.8:1 |
| LPG | 8.2 | 9.9 | 7.5 |
| Aromatics | 8.2 | 4.8 | 6.6 |
| Naphthenes | 2.4 | 3.9 | 2.0 |
| C$_5$+ paraffins | 7.9 | 7.3 | 6.8 |

*N$_2$ dilution
**based on total catalyst weight

The average coking rate is about 1.4 wt. %/day without regeneration. During these runs the coke content of the catalyst increases from 3 wt. % initially to 15, 17.7 and 35.6 %, respectively, at the end of runs. Continuous or periodic withdrawal of a coked catalyst fraction is employed to maintain the desired activity, as measured by the research index (RI), expressed as the propane:-propene ratio. While nitrogen gas is used to demonstrate the effect of a diluent, other gases may be employed to decrease the oxygenate partial pressure, such as steam, hydrogen or light hydrocarbon recycle gas, particularly C$_1$-C$_4$ alkanes.

Methanol breakthrough is observed at high space velocities and/or low RI values. While 98-99.5% conversion is obtainable in the RI range of 0.04 to 0.06, complete conversion is achieved at 0.06 to 0.1 RI.

Figure 3:
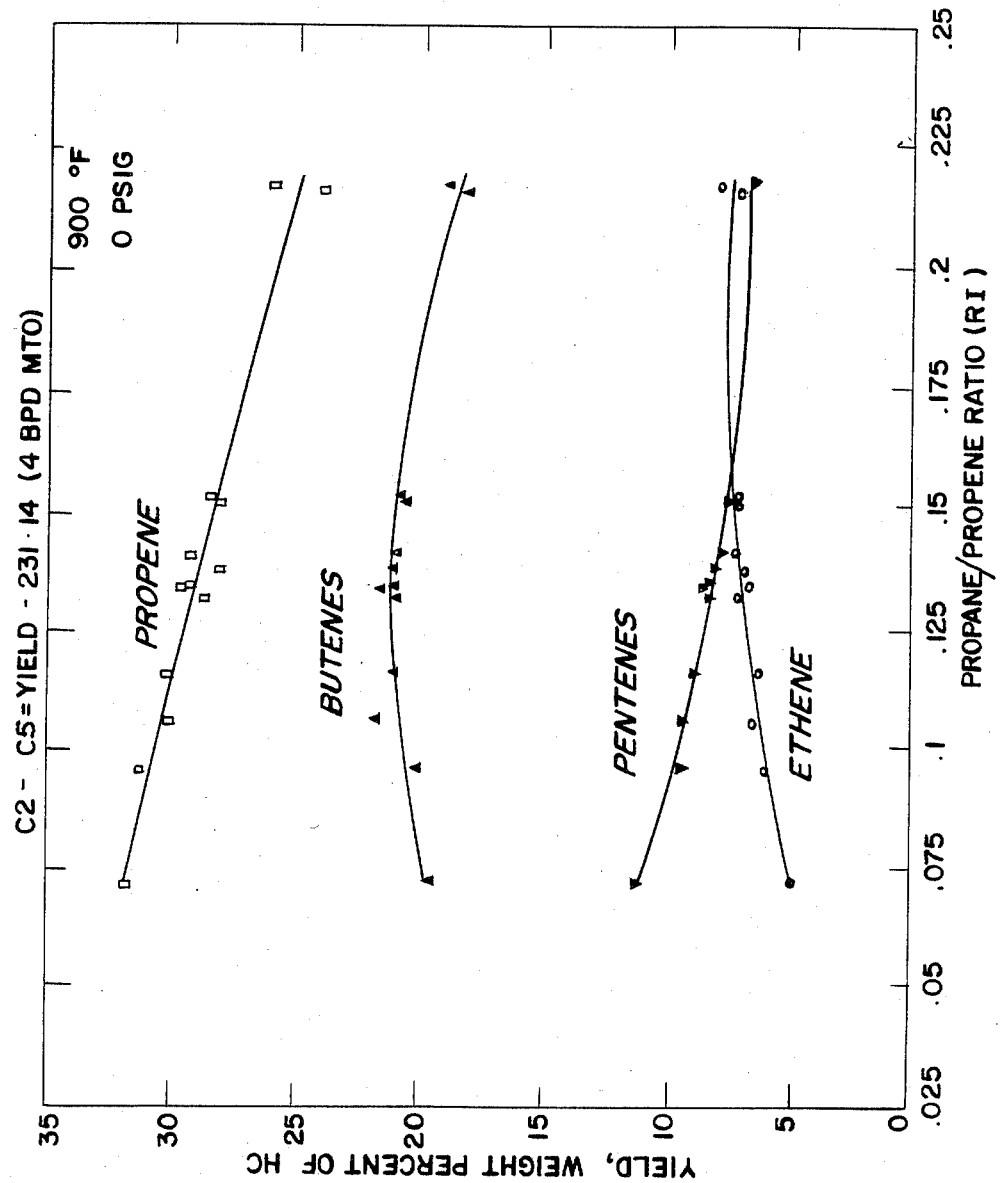
FIG. 3 is a yield plot for the lower olefins vs. propane:propene ratio.
Figure 4:
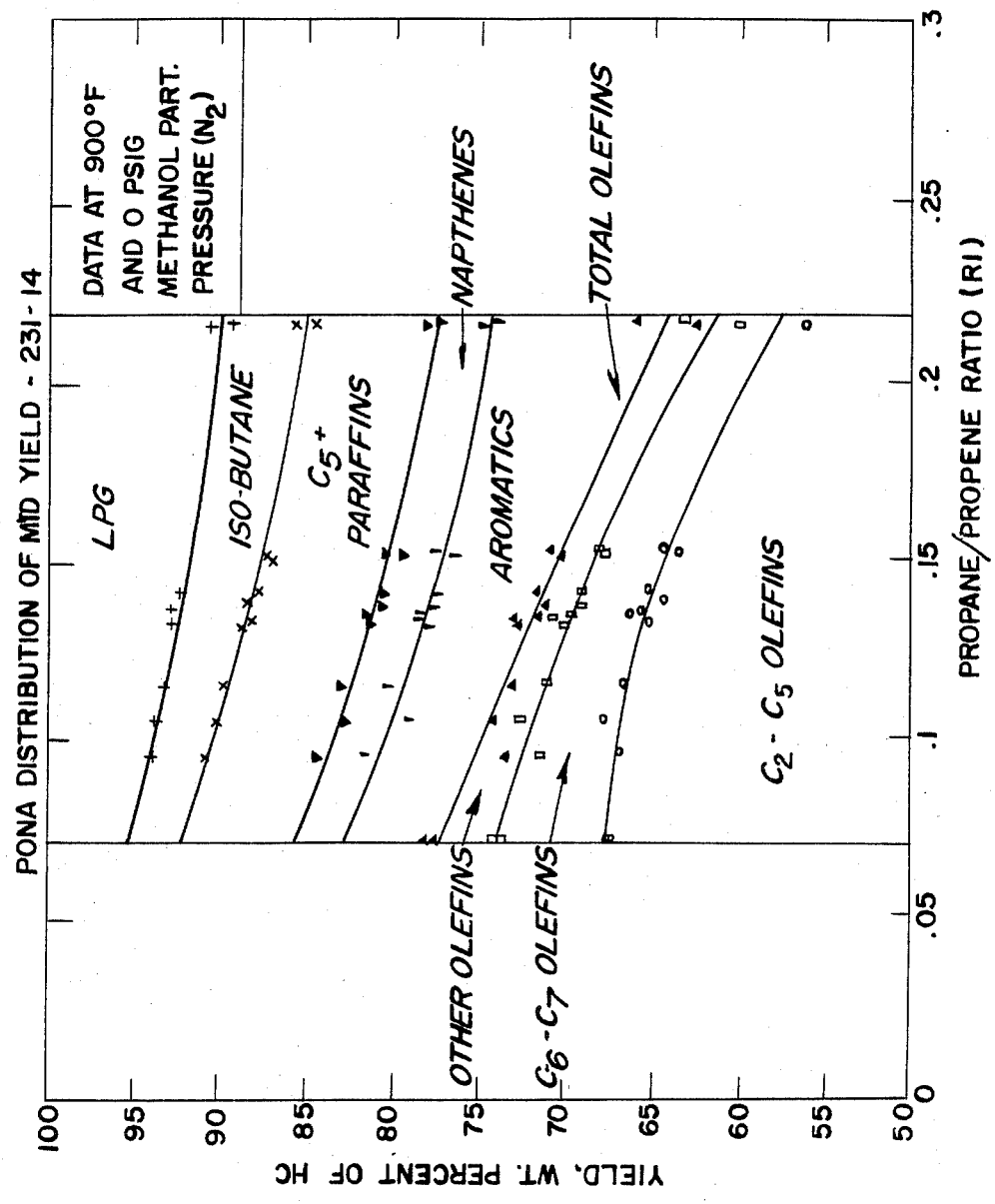
FIG. 4 is a PONA distribution diagram for hydrocarbon product relating to FIG. 3.

The effect of catalysts activity, as measured by propane:propene ratio, is depicted in FIGS. 3 and 4 for a series of runs conducted in the turbulent bed of Examples 1-3 except that average bed temperature is maintained at about 482° C. (900° F.) and methanol partial pressure is maintained at about 100 kPa by N$_2$ addition. FIG. 3 shows hydrocarbon product yield for each of the C$_2$-C$_5$ olefins, while FIG. 4 shows the total product distribution.

Figure 5:
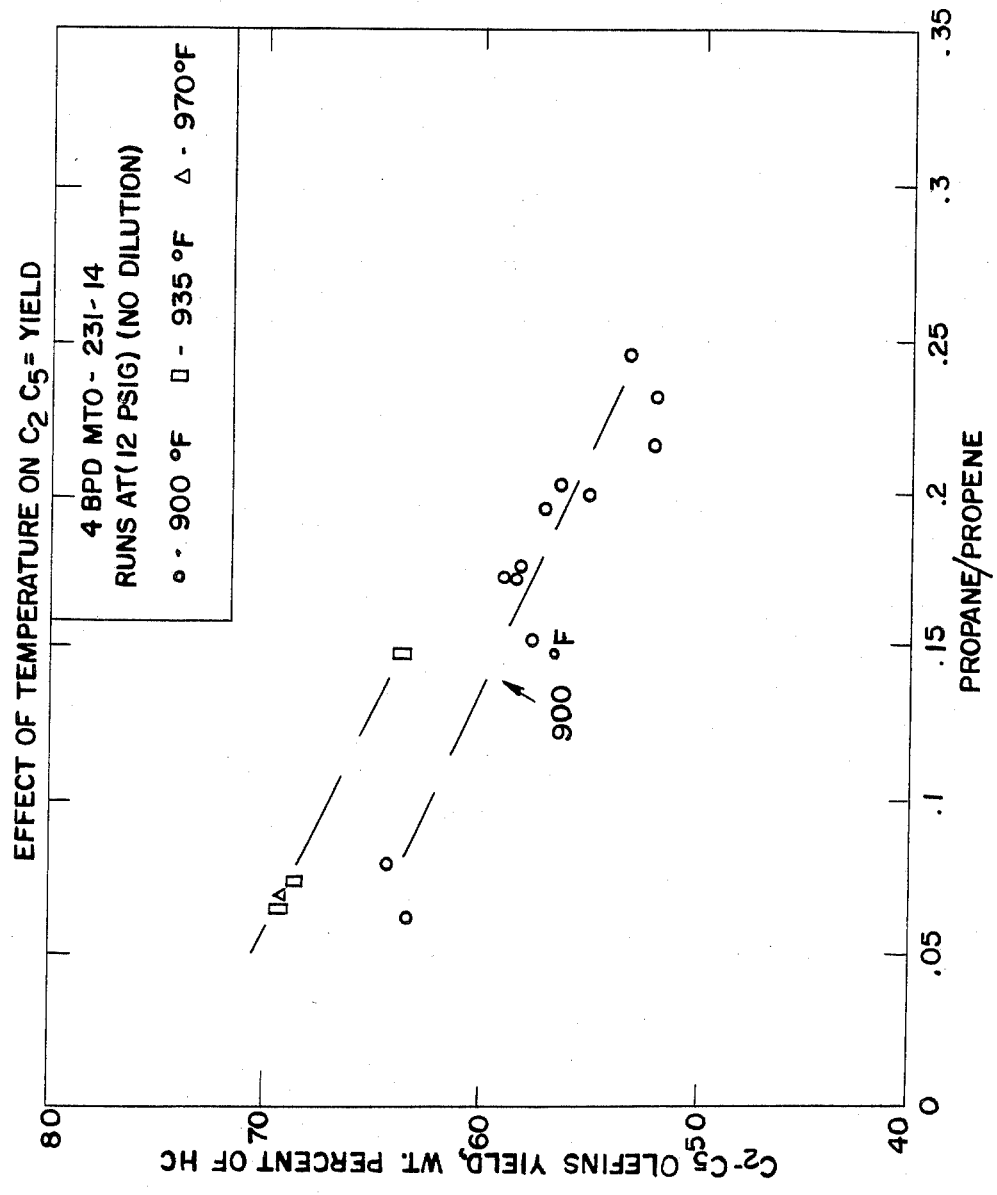
FIG. 5 depicts the effect of reaction temperature on $C_2-C_5$ olefin yield vs. propane:propene ratio.

The effect of process temperature is demonstrated in FIG. 5 for another similar series of runs at 185 kPa using undiluted methanol feedstock. While C$_2$-C$_5$ olefin yield is increased by raising the temperature from 480° to 500° C., a further rise in temperature to 520° C. did not improve these yields.

What is claimed is:

1. A fluidized bed catalytic process for substantially complete conversion of feedstock consisting essentially of methanol and/or dimethylether to hydrocarbons rich in light olefins, comprising the steps of
   maintaining a fluidized bed of zeolite catalyst particles in a turbulent reactor bed at a temperature of at least 475° C., said catalyst having an apparent particle density of about 0.9 to 1.6 g/cm$^3$ and a size range of about 1 to 150 microns, and average catalyst particle size of about 20 to 100 microns containing about 10 to 25 weight percent of fine particles having a particle size less than 32 microns;
   passing hot feedstock vapor upwardly through the fluidized catalyst bed under turbulent flow conditions;
   maintaining turbulent fluidized bed conditions through the reactor bed between transition velocity and transport velocity at a superficial fluid velocity of about 0.3 to 2 meters per second; and
   recovering hydrocarbon product containing a major amount of olefins and having a molar ratio of C$_3$+ olefins to ethene of at least 12:1.

2. A fluidized bed process according to claim 1 wherein the fluidized bed density is about 100 to 300 kg/m$^3$, measured at the bottom of the bed, and wherein the catalyst comprises ZSM-5 type zeolite.

3. The process of claim 1 wherein the feedstock comprises crude methanol which is converted at least 98 weight percent in the turbulent reactor bed, which has a bed height of at least 9 meters.

4. In the process for continuous conversion of methanol and/or dimethylether feedstock to hydrocarbon products consisting predominately of lower olefins wherein the feedstock is contacted at elevated temperature of at least 475° C. with a fluidized bed of zeolite catalyst under conversion conditions, the improvement which comprises
   maintaining the fluidized catalyst bed in a vertical reactor column having a turbulent reaction zone by passing feedstock vapor upwardly through the reaction zone at a velocity greater than dense bed transition velocity to a turbulent regime and less than transport velocity for the average catalyst particle;
   maintaining superficial feedstock vaper velocity at about 0.3-2 m/sec and weight hourly feedstock space velocity (based on methanol equivalent and total reactor catalyst inventory) at about 1 to 3; wherein the average fluidized bed density measured at the reaction zone bottom is about 100 to 300 kg/m$^3$ for zeolite having apparent crystal density of about 0.9 to 1.6 gm/cm$^3$;
   withdrawing a portion of coked catalyst from the reaction zone, oxidatively regenerating the withdrawn catalyst and returning regenerated catalyst to the reaction zone at a rate to control catalyst activity whereby propane:propene molar ratio in the hydrocarbon product is maintained at about 0.04:1 to 0.1:1 under conditions of substantially complete feedstock conversion, thereby producing C$_3$+ olefins at an ethene molar ratio greater than about 12:1.

5. The process of claim 4 wherein the catalyst consists essentially of a medium pore pentasil zeolite having an apparent alpha value of about 3 to 50, and average particle size of about 20 to 100 microns, the reactor catalyst inventory including at least 10 weight percent fine particles having a particle size less than 32 microns.

6. The process of claim 5 wherein the catalyst particles comprise about 5 to 90 weight percent ZSM-5 zeolite having a crystal size of about 1-2 microns.

7. The process of claim 4 wherein the hydrocarbon product contains at least 70 weight percent total olefins, including at least 50 weight percent C$_2$-C$_4$ olefins and not more than 10 weight percent aromatic hydrocarbons.

8. The process of claim 1 wherein the feedstock comprises a major amount of methanol and 0 to 50 mole percent of a diluent gas, and wherein the partial pressure of methanol is about 35 to 240 kPa.

9. The process of claim 8 wherein the product mole ratio of C$_3$+ olefin to ethene is at least 12:1.

* * * * *

UNITED STATES PATENT AND TRADEMARK OFFICE
CERTIFICATE OF CORRECTION

PATENT NO. : 4,547,616

DATED : October 15, 1985

INVENTOR(S) : A. A. Avidan, R. M. Gould, S. E. Kane

It is certified that error appears in the above-identified patent and that said Letters Patent is hereby corrected as shown below:

Column 3, line 25, change "40" to --32--.

Column 6, line 50, change "40" to --32--.

Signed and Sealed this

Fifteenth Day of April 1986

[SEAL]

Attest:

DONALD J. QUIGG

Attesting Officer

Commissioner of Patents and Trademarks